United States Patent [19]

Murai et al.

[11] 4,009,206
[45] Feb. 22, 1977

[54] N-(SUBSTITUTED PHENYL AND BENZYL)ABIETAMIDES

[76] Inventors: Hiromu Murai; Katsuya Ohata; Hiroshi Enomoto; Kenji Sempuku; Koji Kitaguchi; Yukio Fujita; Yoshiaki Yoshikuni; Kohei Kura; Katsahide Saito; Tamiki Mori; Yasuo Yasutomi, all c/o Nippon Shinyaku Co., Ltd., 14 Kisshoin Nishinosho Monguchicho, Minami Kyoto, Japan

[22] Filed: Aug. 13, 1975

[21] Appl. No.: 604,308

[30] Foreign Application Priority Data
Aug. 28, 1974 Japan .............................. 49-99386
Nov. 9, 1974 Japan ............................ 49-129295

[52] U.S. Cl. .................... 260/557 B; 260/471 R; 260/518 R; 260/518 A; 260/519; 260/514.5; 424/309; 424/317; 424/320
[51] Int. Cl.$^2$ ............ C07C 101/18; C07C 101/453; C07C 103/19; A61K 31/16
[58] Field of Search ........ 260/557 B, 468 G, 514.5, 260/471 R, 518 A, 518 R, 519; 424/320

[56] References Cited
UNITED STATES PATENTS
2,201,237  5/1940  Littmann ......................... 260/514.5
3,281,453  10/1966  Weil et al. ................. 260/557 B X OTHER PUBLICATIONS
Kanno, CA 56:7366h (1962).
Geigy A.-G., CA 66:47447d (1967).
Vrbovsky, CA 77:43376j (1972).

*Primary Examiner*—Daniel E. Wyman
*Assistant Examiner*—Thomas A. Waltz

[57] ABSTRACT

Substituted N-phenyl and N-benzyl abietamide derivatives, including the dehydro-, dihydro-, and tetrahydroabietamide derivatives, are cholesterol lowering agents. The abietamide derivatives, of which N-(2,6-dimethylphenyl)-$\Delta^8$-dihydroabietamide is a typical example, are produced by the reaction of abietic acid, dehydroabietic acid, dihydroabietic acid, tetrahydroabietic acid and/or active derivatives thereof with a substituted aniline or benzylamine.

15 Claims, No Drawings

N-(SUBSTITUTED PHENYL AND BENZYL)ABIETAMIDES

DETAILED DESCRIPTION OF THE INVENTION

This invention relates to novel abietamide derivatives having a general formula

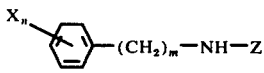

where
- X = halogen, nitro, lower alkyl, haloalkyl, hydroxyl, lower alkoxy, carboxyl, or carboalkoxy; being the same or different
- n = an integer of 1, 2, or 3
- m = an integer of 0 or 1
- Z = abietic, dehydroabietic, dihydroabietic, or tetrahydroabietic acid residue and a method of production thereof. More particularly this invention relates to anilide and benzylamide derivatives of abietic acid and related compounds and, furthermore particularly, this invention relates to abietanilides (hereinafter referred to as AAN), dehydroabietanilides (DEAN), dihydroabietanilides (DIAN), tetrahydroabietanilides (TAN), abietic acid benzylamide derivatives (ABA), dehydroabietic acid benzylamide derivatives (DEBA), dihydroabietic acid benzylamide derivatives (DIBA), and tetrahydroabietic acid benzylamide derivatives (TBA) and manufacture thereof by the reaction of abietic acid (AA), dehydroabietic acid (DEA), dihydroabietic acid (DIA), tetrahydroabietic acid (TA), and/or active derivatives thereof with a compound of a formula

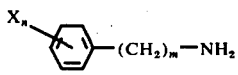

where definitions for X, n, and m are the same as defined above.

The abietic acid series compounds particularly AA which is one of the starting materials according to this invention is contained in large quantities in the resin obtainable from the pine varieties plants and is one of the readily and inexpensively available natural compounds. DEA can also be obtained with high yield by treating the pine variety resin with palladium carbon. DIA and TA can be readily prepared from AA by the use of a suitable reducing agent.

The term "active derivatives" of abietic acid, etc. means acid anhydride, acid esters, and acid halides. Derivation of acids to such active derivatives can be done by the usual way. For instance, acid anhydride is prepared by the use of dehydrating agents such as acetic anhydride and acetyl chloride; acid esters are prepared through the ordinary esterification such as, for example, methyl esterification with diazomethane; and acid halides are prepared through halogenation using such compounds as $PX_5$, $PX_3$, and $SOX_2$ where X means halogen atom.

Aniline and benzylamine compounds (II) are other starting materials in this invention. Examples of such compounds covered by the formula (II) are 2,6-dimethylaniline; 2,4-dimethylaniline; 2,4,6-trimethylaniline; o-ethoxycarbonylaniline; p-methoxycarbonylaniline; 3-hydroxy-4-carboxyaniline; m-trifluoromethylaniline; p-chloroaniline; m-bromoaniline; p-ethoxyaniline; p-methoxyaniline; o-methylbenzylamine; m-methylbenzylamine; p-methylbenzylamine; p-methoxybenzylamine; o-chlorobenzylamine; m-chlorobenzylamine; and p-chlorobenzylamine. It should, however, be understood that this invention is not limited to the use of the above compounds only.

Novel compounds (I) according to this invention are prepared by, for example, the method referred to above. If necessary, the reaction may be carried out using a dehydrating agent such as dicycloalkylcarbodiimide or a basic catalyst such as alkali hydroxides, alkoxides, and amides.

Regarding the solvent for the reaction, alcohols such as methanol and ethanol, fatty or aromatic hydrocarbons such as n-hexane, benzene and xylene, halogenated hydrocarbons such as chloroform, cyclic ethers such as dioxane and tetrahydrofuran and aromatic heterocyclic compounds represented by pyridine can be used. The reaction may sometimes readily proceed without solvent, and in such case the solvent may be dispensed with.

Regarding the proportions of the materials used, 1.5 to 3 mols of the compound (II) are usually added to one mole of abietic acids of their active derivatives such as acid anhydride, ester and acid halide. If necessary, the acid component is dissolved or suspended in an adequate quantity of a suitable solvent, and the compound (II) is added by small quantities while executing requisite cooling and agitation of the system.

The reaction is carried out under a suitable temperature condition, for instance under ice cooling state, at room temperature or under heating, and is usually completed within 12 hours. Particularly the reaction between acid halide and compound (II) is completed at lower temperature within one hour, and this can be readily recognized from the disappearance of spots of material on a silica gel thin layer chromatogram.

After the termination of the reaction, the intended abietamide derivatives (I) such as AAN, DEAN, DIAN, TAN, ABA, DEBA, DIBA, and TBA can be separated from the reaction product mixture by the usual way. For example, where a hydrophilic solvent is used for reaction, the solvent is first removed under a reduced pressure condition, and a hydrophobic solvent such as ether and benzene is newly added. Then, the resultant system is washed. In case where a hydrophobic solvent such as benzene and n-hexane is used, the system is directly washed. The washing is made with a 3 to 5 percent dilute acid, if necessary, and then with a 3 to 5 percent dilute alkali and thereafter with water, followed by drying. After drying, the residual solvent is removed from the system, whereby crystalline particles as residue are obtained in many cases. In this case, purification through re-crystallization is directly made by using a suitable re-crystallizing solvent. Where the residue after the removal of solvent is oily, the purification is made with alumina or silica gel column chromatography or thin layer chromatography for manufacture.

While the DIA disclosed in the examples is $\Delta^8$-dihydroabietic acid, this invention is not limited to the use of it only, but other $\Delta^7$-, $\Delta^{13}$-, and $\Delta^{14}$-isomers are, of course, used as well.

The following examples are given to illustrate some representative embodiments of the invention. It is to be understood, however, that these examples are for the purpose of illustration only and not to be construed as a limit on the invention.

Examples 1 to 5 relate to manufacture of anilide derivatives or Formula 1 where $M = 0$ and Examples 6 to 10 to manufacture of benzylamine derivatives of Formula 1 where $M = 1$.

EXAMPLE 1

N-(2,6-dimethylphenyl)-$\Delta^8$-dihydroabietamide was produced in the following way:

Acid chloride obtained from 6.1 grams (20 millimols) of $\Delta^8$-DIA and excessive thionyl chloride was cooled to freeze, and then 4.84 grams (20 millimols) of 2,6-dimethylaniline was added.

The resultant system was left at room temperature for one hour while intermittently agitating it. To the resultant liquid 50 millilitres of benzene was added to form a suspension, which was then washed with 5% HCl and then with water. Then, the benzene layer was dried with anhydrous magnesium sulfate, followed by removal of benzene. The resultant crystalline residue was re-crystallized from acetone to obtain 5.2 grams of colorless needle-like crystals (corresponding to a yield of 80 percent) with a melting point of 200° to 202° c.

Analysis of element: $C_{28}H_{41}ON$

| Analysis of element: | $C_{28}H_{41}ON$ | | |
|---|---|---|---|
| | C | H | N |
| Calculated (%) | 82.50 | 10.14 | 3.44 |
| Found (%) | 82.38 | 10.22 | 3.37 |

EXAMPLE 2

N-(2,6-dimethylphenyl)-tetrahydroabietamide was produced in the following way:

Acid chloride obtained from 1.53 grams (5 millimols) of TA and excessive thionyl chloride was added to 10 millilitres of benzene, and to the resultant system 1.82 grams (15 millimols) of 2,6-dimethylaniline was gradually added. Then, the resultant system was continually agitated at room temperature for 2 hours, and then the precipitate was filtered away. Then, the resultant liquid was washed with 5-% HCl and then with water, and then the benzene layer was dried with anhydrous magnesium sulfate.

Then, benzene was removed to obtain a crystalline residue, which was then re-crystallized from acetone to obtain 16.8 grams of colorless needle-like crystals (corresponding to a yield of 82 percent) with a melting point of 218° to 220° C.

Analysis of element: $C_{28}H_{43}ON$

| Analysis of element: | $C_{28}H_{43}ON$ | | |
|---|---|---|---|
| | C | H | N |
| Calculated (%) | 82.09 | 10.58 | 3.42 |
| Found (%) | 82.13 | 10.45 | 3.60 |

EXAMPLE 3

N-(p-ethoxyphenyl)-$\Delta^8$-dihydroabietamide was produced in the following way:

Methylester obtained from 3.05 grams (10 millimols) of $\Delta^8$-DIA and excessive diazomethane was added to 20 millilitres of xylene, and to the resultant system 2.8 grams (20 millimols) of p-ethoxyaniline and 830 millimols (25 millimols) of sodium amide were added. The resultant liquid was filtered, and the filtrate was washed with 5-% HCl and then with water, and then the xylene layer was dried with anhydrous magnesium sulfate, followed by filtering. Then, xylene was removed under reduced pressure, and the crystalline residue powder was re-crystallized from methanol to obtain 17.8 grams of colorless needle-like crystals (corresponding to a yield of 42 percent) with a melting point of 136° to 138° C.

| Analysis of element: | $C_{28}H_{41}O_2N$ | | |
|---|---|---|---|
| | C | H | N |
| Calculated (%) | 79.38 | 9.76 | 3.31 |
| Found (%) | 79.44 | 9.51 | 3.12 |

EXAMPLE 4

N-(p-methoxyphenyl)-abietamide was produced in the following way:

5.86 grams (10 millimols) of AA anhydride, 3.70 grams (30 millimols) of p-methoxy aniline and 50 millilitres of ethanol were mixed together, and the resultant liquid was agitated under heating for 2 hours. Then, ethanol was removed under reduced pressure. Then, 50 millilitres of ether was added, and the ether layer was washed with 3-% KOH aquaous solution, with 3-% HCl and then with water. Then, the resultant ether layer was dried with anhydrous magnesium sulfate, followed by filtering to remove ether. The resultant oily residue was left to crystallize. Then, by recrystallizing from ethanol 1.23 grams of colorless small needle-like crystals (corresponding to a yield of 60.6 percent) with a melting point of 134° to 136° C were obtained.

| Analysis of element: | $C_{27}H_{37}O_2N$ | | |
|---|---|---|---|
| | C | H | N |
| Calculated (%) | 79.56 | 9.15 | 3.44 |
| Found (%) | 79.60 | 9.16 | 3.18 |

EXAMPLE 5

N-(p-chlorophenyl)-dehydroabietamide was produced in the following way:

3.00 grams (10 millimols) of DEA, 1.53 grams (12 millimols) of p-chloroaniline, 24.8 grams (12 millimols) of dicyclohexylcarbodiimide and 30 millilitres of dry dioxane were mixted together, and the resultant liquid was agitated at room temperature for 6 hours and then heated at 60° C for one hour. Then, the dioxane was removed through concentration under reduced pressure. Then, 150 millilitres of methylene chloride was added to the resultant residue, and the methylene chloride layer was washed with 3-% HCl and then with water, followed by drying with anhydrous sodium sulfate and filtering. The resultant filtrate was concentrated to 40 millilitres, followed by leaving overnight at room temperature. Then the precipitate was filtered away, and the filtrate was concentrated to dry solide. The powdery residue thus obtained was then re-crystallized from ethanol to obtain 3.03 grams of colorless needle-like crystals (corresponding to a yield of 74 percent) with a melting point of 180° to 181.5° C.

| Analysis of element: | $C_{26}H_{32}ONCl$ | | | |
|---|---|---|---|---|
| | C | H | N | Cl |
| Calculated (%) | 76.17 | 7.87 | 3.42 | 8.62 |
| Found (%) | 76.18 | 8.14 | 3.54 | 8.54 |

Similar to the above Examples 1 to 5, the following compound were also produced as further examples:

N-(2-Methylphenyl)-dihydroabietamide with a melting point of 164°–166° C

N-(2-Ethylphenyl)-dihydroabietamide with a melting point of 167°–169° C

N-(2,6-dimethylphenyl)-dehydroabietamide with a melting point of 227° to 229° C

N-(2,4-dimethylphenyl)-dihydroabietamide with a melting point of 148° to 150° C

N-(2,6-Diethylphenyl)-dihydroabietamide with a melting point of 219° to 221° C

N-(o-ethoxycarbonylphenyl)-dihydroabietamide which is oily

N-(p-methoxycarbonylphenyl)-dihydroabietamide with a melting point of 152° to 154° C N-(3-hydroxy-4-carboxyphenyl)-dihydroabietamide with a melting (or decomposing) point of 260° C N-(m-trifluoromethylphenyl)-dihydroabietamide with a melting point of 137° to 138° C N-(m-bromophenyl)-dihydroabietamide with a melting point of 107° to 109° C N-(p-nitrophenyl)-dihydroabietamide which is oily N-(m-methoxyphenyl)-dihydroabietamide with a melting point of 149° to 152° C N-(2,4,6-trimethylphenyl)-dihydroabietamide with a melting point of 215° to 217° C

EXAMPLE 6

N-(2-methylbenzyl)-$\Delta^8$-dihydroabietamide was produced in the following way:

Acid chloride obtained from 1.53 grams (5 millimols) of $\Delta^8$-DIA and excessive thionyl chloride was dissolved in 10 millilitres of benzene, and to this solution a solution obtained by dissolving 1.87 grams (15 millimols) of o-methylbenzylamine in 10 millilitres of benzene was added under cooling condition. The resultant system was the agitated at room temperature for 1.5 hours. The resultant liquid was then washed with 5-% HCl, water and with 5-% sodium hydroxide aqueous solution in the mentioned order. Then, the benzene layer was dried with anhydrous magnesium sulfate, followed by removal of benzene. The resultant crystalline residue was re-crystallized from acetone to obtain 1.69 grams of colorless planar crystals (corresponding to a yield of 83 percent) with a melting point of 121° to 122° C.

| Analysis of element: | $C_{28}H_{41}ON$ | | |
|---|---|---|---|
| | C | H | N |
| Calculated (%) | 82.50 | 10.14 | 3.44 |
| Found (%) | 82.45 | 10.29 | 3.52 |

EXAMPLE 7

N-(3-chlorobenzyl)-$\Delta^8$-dihydroabietamide was produced in the following way: Acid chloride obtained from 1.53 grams (5 millimols) of $\Delta^8$-DIA and excessive thionyl chloride was dissolved in 10 millilitres of benzene, and to this solution a solution obtained by dissolving 2.12 grams (15 millimols) of m-chlorobenzylamine in 10 millilitres of benzene was added under cooling condition. The resultant system was then agitated at room temperature for 3 hours. The resultant liquid was then treated in the same manner as in Example 6, and through re-crystallization from methanol 1.68 grams of colorless needle-like crystals (corresponding to a yield of 79 percent) with a melting point of 116° to 117° C were obtained.

| Analysis of element: | $C_{27}H_{38}ONCl$ | | | |
|---|---|---|---|---|
| | C | H | N | Cl |
| Calculated (%) | 75.76 | 8.94 | 3.27 | 8.28 |
| Found (%) | 75.72 | 9.05 | 3.47 | 8.30 |

EXAMPLE 8

N-(4-methoxybenzyl)-abietamide was produced in the following way:

5.89 grams (10 millimols) of AA anhydride, 3.42 grams (25 millimols) of p-methoxybenzylamine and 50 millilitres of ethanol were mixed together, and the resultant liquid was agitated while heating for 1.5 hours. Then, ethanol was removed under reduced pressure, and then 50 millilitres of ether was added.

The ether layer thus formed was then washed with 3-% KOH aqueous solution, water and with 3-% HCl in the mentioned order, and then it is dried with anhydrous magnesium sulfate, followed by removal of ether through filtering. The resultant oily residue was subjected to silica gel column chromatography with chloroform used as solvent to obtain 4.22 grams of glassy substance (corresponding to a yield of 72 percent).

| Analysis of element: | $O_{23}H_{39}O_2N$ | | |
|---|---|---|---|
| | C | H | N |
| Calculated (%) | 79.76 | 9.32 | 3.32 |
| Found (%) | 79.68 | 9.27 | 3.40 |

EXAMPLE 9

N-(2-methylbenzyl)-tetrahydroabietamide was produced in the following way:

3.06 grams (10 millimols) of TA, 1.50 grams (12 millimols) of p-methylbenzylamine, 2.48 grams (12 millimols) of dicyclohexylcarbodiimide and 30 millilitres of dry dioxane were mixed together, and the resultant liquid was agitated at room temperature for 6 hours and then heated at 60° C for one hour. Then, the dioxane was removed through concentration under reduced pressure, and 150 millilitres of methylene chloride was added to the residue. The methylene chloride layer thus formed was then washed with 3-% HCl and then with water and dried with anhydrous magnesium sulfate, followed by filtering. The filtrate was then concentrated to 40 millilitres, followed by leaving overnight at room temperature. Then, the precipitate was filtered away, and the filtrate was concentrated to dry solide. The crystalline residue thus obtained was re-crystallized from methanol to obtain 2.65 grams colorless needle-like crystals (corresponding to a yield of 65 percent) with a melting point of 159° to 161° C.

| Analysis of element: | $C_{28}H_{43}ON$ | | |
|---|---|---|---|
| | C | H | N |
| Calculated (%) | 82.09 | 10.58 | 3.42 |
| Found (%) | 82.14 | 10.58 | 3.58 |

EXAMPLE 10

N-(4-methylbenzyl)-dehydroabietamide was produced in the following way:

Methylester obtained from 3.00 grams (10 millimols) of DEA and excessive diazomethane was added to 20 millilitres of xylene, and to the resultant system 2.74 grams (30 millimols) of p-methylbenzylamine and 830 milligrams (25 millimols) of sodium amide were added. The resultant liquid was sealed within a pressure-bearing tube and heated there at 180° C for 20 hours. The resultant liquid was then filtered, and the filtrate was washed with 5-% HCl and then with water. The xylene layer was then dried with anhydrous magnesium sulfate and then filtered, followed by removal of xylene under reduced pressure. The crystalline residue was then re-crystallized from methanol to obtain 1.78 grams of colorless needle-like crystals (corresponding to a yield of 44 percent) with a melting point of 124° to 126° C.

| Analysis of element: | $C_{28}H_{37}ON$ | | |
|---|---|---|---|
| | C | H | N |
| Calculated (%) | 83.32 | 9.24 | 3.47 |
| Found (%) | 83.29 | 9.33 | 3.50 |

Similar to the above Example 6 to 10, the following compounds were also produced as further examples:

N-(3-methylbenzyl)-$\Delta^8$-dihydroabietamide with a melting point of 105° to 110° C N-(4-methylbenzyl)-$\Delta^8$-dihydroabietamide with a melting point of 130° to 132° C N-(4-methoxybenzyl)-$\Delta^8$-dihydroabietamide with a melting point of 129° to 130° C N-(2-chlorobenzyl)-$\Delta^8$-dihydroabietamide with a melting point of 150° to 151° C N-(4-chlorobenzyl)-$\Delta^8$-dihydroabietamide with a melting point of 127° to 130° C Compounds prepared according to this invention have a high activity of reducing cholesterol in blood, which can be proved by an experiment described below.

A completely synthetic diet containing 1% of cholesterol, 0.25% of sodium cholate and 0.0003%, 0.003%, and 0.03% of the test compound is given to a group of 6 male rats having a body weight of about 50 g consecutively for 3 days, and the rats are fasted overnight. Then, the rats are decapitated and blood is collected to determine the cholesterol concentration in blood. The concentration of cholesterol in blood is measured with Technicon Autoanalyzer(Technicon Laboratory: Method File N-24a) Obtained results are shown in Table 1.

Table 1

| Compound | % Inhibition Dose in Diet | | |
|---|---|---|---|
| | 0.0003% | 0.003% | 0.03% |
| N-(m-Bromophenyl)-dihydroabietamide | 7 | 23* | 60** |
| N-(2,6-Dimethylphenyl)-$\Delta^8$-dihydroabietamide | 33** | 76** | 102** |
| N-(2,4,6-Trimethylphenyl)-dihydroabietamide | 21** | 54** | 70** |
| N-(4-Chlorobenzyl)-$\Delta^8$-dihydroabietamide | — | 9 | 30** |

Each value shown in the Table is a relative value determined based on the supposition that the value of the control group (the cholesterol-administered group) is 0 and the value of the normal group (the non-cholesterol-administered group) is 100. The mark "*" indicates that the value is statistically significant over the control group with a significant level of 5% and the mark "**" indicates that the value is statistically significant over the control group with a significance level of 1%.

From the results shown in the Table, it will readily be understood that each compound has a significant effect of reducing cholesterol in blood even when it is administered in a very minute amount and is very valuable as an anti-arteriosclerotic agent.

What is claimed is:

1. An N-(substituted phenyl) or N-(substituted benzylamide of an acid selected from the group consisting of abietic, dehydroabietic, dihydroabietic and tetrahydroabietic acids wherein said phenyl or benzyl is substituted with from one to three substituents independently selected from the group consisting of halo, nitro, lower alkyl, haloalkyl, hydroxyl, lower alkoxy, carboxyl or carbalkoxy.

2. An amide according to claim 1 wherein said substituted phenyl is chlorophenyl, bromophenyl, nitrophenyl, methylphenyl, dimethylphenyl, trimethylphenyl, ethylphenyl, diethylphenyl, trifluoromethylphenyl, methoxyphenyl, ethoxyphenyl, hydroxy-carboxyphenyl, carbomethoxyphenyl or carbethoxyphenyl.

3. The amide of abietic acid, dehydroabietic acid, $\Delta^8$-dihydroabictic acid or tetrahydroabietic acid according to claim 3.

4. An amide according to claim 1 wherein said substituted benzyl is chlorobenzyl, methylbenzyl, or methoxybenzyl.

5. The amide of abietic acid, dehydroabietic acid, $\Delta^8$-dihydroabietic acid or tetrahydroabietic acid according to claim 4.

6. The amide according to claim 1 which is N-(2,6-dimethylphenyl)-$\Delta^8$-dihydroabietamide.

7. The amide according to claim 1 which is N-(2,6-dimethylphenyl)-tetrahydroabietamide.

8. The amide according to claim 1 which is N-(p-ethoxyphenyl)-$\Delta^8$-dihydroabietamide.

9. The amide according to claim 1 which is N-(p-methoxyphenyl)-abietamide.

10. The amide according to claim 1 which is N-(p-chlorophenyl)-dehydroabietamide.

11. The amide according to claim 1 which is N-(2-methylbenzyl)-$\Delta^8$-dihydroabietamide.

12. The amide according to claim 1 which is N-(3-chlorobenzyl)-$\Delta^8$-dihydroabietamide.

13. The amide according to claim 1 which is N-(4-methoxybenzyl)-abietamide.

14. The amide according to claim 1 which is N-(2-methylbenzyl)-tetrahydroabietamide.

15. The amide according to claim 1 which is N-(4-methylbenzyl)-dehydroabietamide.

* * * * *